United States Patent
Baek et al.

(10) Patent No.: US 11,041,181 B2
(45) Date of Patent: Jun. 22, 2021

(54) PROMOTER AND METHOD FOR PRODUCING PURINE NUCLEOTIDE USING THE SAME

(71) Applicant: CJ CHEILJEDANG CORPORATION, Seoul (KR)

(72) Inventors: Min Ji Baek, Suwon-si (KR); Ji Hye Lee, Anyang-si (KR); So Jung Park, Suwon-si (KR); Jee Yeon Bae, Suwon-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 16/487,721

(22) PCT Filed: Apr. 8, 2019

(86) PCT No.: PCT/KR2019/004119
§ 371 (c)(1),
(2) Date: Oct. 26, 2020

(87) PCT Pub. No.: WO2020/175735
PCT Pub. Date: Sep. 3, 2020

(65) Prior Publication Data
US 2021/0047665 A1   Feb. 18, 2021

(30) Foreign Application Priority Data
Feb. 26, 2019   (KR) .................. 10-2019-0022546

(51) Int. Cl.
*C12P 19/32* (2006.01)
*C12N 9/00* (2006.01)
*C12N 15/77* (2006.01)

(52) U.S. Cl.
CPC ............... *C12P 19/32* (2013.01); *C12N 9/93* (2013.01); *C12N 15/77* (2013.01); *C12Y 603/04004* (2013.01)

(58) Field of Classification Search
None
See application file for complete search history.

(56) References Cited

U.S. PATENT DOCUMENTS

2020/0377917 A1   12/2020   Baek et al.

FOREIGN PATENT DOCUMENTS

| KR | 10-1904675 B1 | 9/2018 |
| KR | 10-1950141 B1 | 2/2019 |

OTHER PUBLICATIONS

GenBank: AB003160.1, "Corynebacterium ammoniagenes purA gene for adenylosuccinate synthetase, complete cds," (2 pages), Jan. 15, 2000.
Qian et al., "Nucleotide mutations in *purA* gene and *pur* operon promoter discovered in guanosine- and inosine-producing *Bacillus subtilis* strains," Biotechnol Letters 28(12):937-941 (2006).
Abbouni et al., "Overproduction of NAD+ and 5'-inosine monophosphate in the presence of 10 uM $^{Mn2+}$ by a mutant of *Corynebacterium ammoniagenes* with thermosensitive nucleotide reduction ($nrd^{ts}$) after temperature shift," Arch Microbiol 182:119-125 (2004).
Ledesma-Amaro et al., "Increased production of inosine and guanosine by means of metabolic engineering of the purine pathway in *Ashbya gossypii*," Microbial Cell Factories 14(58):1-8 (2015).
Peifer et al., "Metabolic engineering of the purine biosynthetic pathway in *Corynebacterium glutamicum* results in increased intracellular pool sizes of Imp and hypoxanthine," Microbial Cell Factories 11(138):1-14 (2012).

*Primary Examiner* — Kagnew H Gebreyesus
(74) *Attorney, Agent, or Firm* — Seed IP Law Group LLP

(57) ABSTRACT

The present disclosure relates to a polynucleotide having a novel promoter activity, a composition for expressing a gene comprising the polynucleotide, a microorganism comprising the gene, and a method for preparing purine nucleotides using the microorganism.

12 Claims, No Drawings
Specification includes a Sequence Listing.

SEQUENCE LISTING

```
<160> NUMBER OF SEQ ID NOS: 25

<210> SEQ ID NO 1
<211> LENGTH: 200
<212> TYPE: DNA
<213> ORGANISM: Unknown
<220> FEATURE:
<223> OTHER INFORMATION: purA promoter WT

<400> SEQUENCE: 1
ggcaaaattg ccgccgcagc ttcatcgatt attttcagtt cttgacgcgt cggaatcgcc      60
gatacctggt gatattcaac atctggcacc gggacatcac cgcagcgcaa aatacgaact     120
tgcatggcta aatacattat cactggcgat aaaggtagag ttaacgcgta tttagcctta     180
aatctaggaa gtgaataacc                                                 200

<210> SEQ ID NO 2
<211> LENGTH: 200
<212> TYPE: DNA
<213> ORGANISM: Unknown
<220> FEATURE:
<223> OTHER INFORMATION: purA modified promoter (a189t)

<400> SEQUENCE: 2
ggcaaaattg ccgccgcagc ttcatcgatt attttcagtt cttgacgcgt cggaatcgcc      60
gatacctggt gatattcaac atctggcacc gggacatcac cgcagcgcaa aatacgaact     120
tgcatggcta aatacattat cactggcgat aaaggtagag ttaacgcgta tttagcctta     180
aatctaggta gtgaataacc                                                 200

<210> SEQ ID NO 3
<211> LENGTH: 200
<212> TYPE: DNA
<213> ORGANISM: Unknown
<220> FEATURE:
<223> OTHER INFORMATION: purA modified promoter (c143t)

<400> SEQUENCE: 3
ggcaaaattg ccgccgcagc ttcatcgatt attttcagtt cttgacgcgt cggaatcgcc      60
gatacctggt gatattcaac atctggcacc gggacatcac cgcagcgcaa aatacgaact     120
tgcatggcta aatacattat cattggcgat aaaggtagag ttaacgcgta tttagcctta     180
aatctaggaa gtgaataacc                                                 200

<210> SEQ ID NO 4
<211> LENGTH: 200
```

<212> TYPE: DNA
<213> ORGANISM: Unknown
<220> FEATURE:
<223> OTHER INFORMATION: purA modified promoter (c143t, a189t)

<400> SEQUENCE: 4

```
ggcaaaattg ccgccgcagc ttcatcgatt attttcagtt cttgacgcgt cggaatcgcc    60
gatacctggt gatattcaac atctggcacc gggacatcac cgcagcgcaa aatacgaact   120
tgcatggcta aatacattat cattggcgat aaaggtagag ttaacgcgta tttagcctta   180
aatctaggta gtgaataacc                                               200
```

<210> SEQ ID NO 5
<211> LENGTH: 1500
<212> TYPE: DNA
<213> ORGANISM: Unknown
<220> FEATURE:
<223> OTHER INFORMATION: purF

<400> SEQUENCE: 5

```
gtggtgaaca ctactttccc cagcgacgtg aatttagatg accaaggcga gcaagaaccc    60
cgcgaagagt gcggtgtctt tggcgtctgg gctcctggtg aagatgttgc gacactgacc   120
tactttggtc tgttcgcatt gcagcatcgt gggcaggaag ctgcaggtat cggcgtcggt   180
gatggagacc gcctcgttgt cttcaaagac atgggcttgg tctcgaatat tttcgatgag   240
tccattttaa attccctcca tggctccgtg ggcgtggggc atacgcgcta ctcgactgcc   300
ggtggcaaag agtggtcgaa tgtccagccg atgtttaata ccacctcaaa tggggtagac   360
atcgctttgt gccacaacgg caacttggtg aactaccaag aactgcgcga tgaagcagta   420
gctctgggac tttaccgaga gaatgaaaaa tccctgtcgg attccatgat catgacagct   480
ttgctggcgc acggagtcgg ggaaggcaac tctgtctttg acgccgctaa gcaactgctg   540
ccaagcatca aggcgctttt tgcttgacc tttaccgatg gcaagacctt gtacgccgcg   600
cgtgacccgc acggtgtacg ccccttggtc attggccgct ggcgcaaggc ctgggttgtt   660
gcttccgaaa cctgtgcgct ggatatcgtg ggcgcacagt ttatccgtga ggtagagccc   720
ggtgaactta tctctgtcaa tgaggcagga atccacagcg aaaaattcgc tgagccgaag   780
cgccagggct gcgtctttga atacgtctac ttggcacgtc cagacaccgt gatcaaaggc   840
cgcaacgttc acgcgacgcg cgtggatatt ggtcgcgcac ttgcgaaatc tcaccctgcg   900
ccagaagctg acatggtcat ccccgtgcca gaatccggaa acccggcagc tgttggctac   960
gcccgggaat cgggcctgac atttgcgcac ggcttggtca aaaacgccta cgtgggtcga  1020
accttcattc agcccaccca gaccttgcgc cagctgggta ttcgcctcaa gctcaacccc  1080
ctgcgcgagg tcatcgaggg caagtcactc gttgttgtag atgactctat tgtccgcggc  1140
aacacccaac gcgcgctggt gcgcatgctg cgtgaagcag cgctgctga agtgcacgtg  1200
cgcattgctt caccgccagt caaatggcct tgtttctacg gcattgactt cgcctcgcct  1260
ggtgaattga ttgctaatat caagccttct gatgatcctc aggtagtaac cgatgcagtg  1320
tgcgaagcta tcggagcaga ctcttttaggg tttgtatctg tagatgagat ggttgaggca  1380
acgcaccaac ctatcaattc cttgtgtacc gcttgctttg atggcaacta cgaactcgga  1440
cttccgaccg ctaaccccaa tgctgacgct gtgcgaactt tgctcagcca aaagaactga  1500
```

<210> SEQ ID NO 6
<211> LENGTH: 29
<212> TYPE: DNA

<213> ORGANISM: Artificial Sequence
<220> FEATURE:
<223> OTHER INFORMATION: purF g1a-1

<400> SEQUENCE: 6
gctctagacc actctaagac gcggccacc                                29

<210> SEQ ID NO 7
<211> LENGTH: 37
<212> TYPE: DNA
<213> ORGANISM: Artificial Sequence
<220> FEATURE:
<223> OTHER INFORMATION: purF g1a-2

<400> SEQUENCE: 7
aagtagtgtt caccatgacg ctgattctac taagttt                       37

<210> SEQ ID NO 8
<211> LENGTH: 38
<212> TYPE: DNA
<213> ORGANISM: Artificial Sequence
<220> FEATURE:
<223> OTHER INFORMATION: purF g1a-3

<400> SEQUENCE: 8
agtagaatca gcgtcatggt gaacactact ttccccag                      38

<210> SEQ ID NO 9
<211> LENGTH: 29
<212> TYPE: DNA
<213> ORGANISM: Artificial Sequence
<220> FEATURE:
<223> OTHER INFORMATION: purF g1a-4

<400> SEQUENCE: 9
gctctagact gtgcgcccac gatatccag                                29

<210> SEQ ID NO 10
<211> LENGTH: 1821
<212> TYPE: DNA
<213> ORGANISM: Artificial Sequence
<220> FEATURE:
<223> OTHER INFORMATION: guaB

<400> SEQUENCE: 10
atgaccgaaa atcgtgtttc taccggtgga gatgacccaa ataaggttgc attgcatggc    60
ttgacgtttg atgacgtgct gctgctacct gccgaatcca atgttgttcc gtcggaagta   120
gacacttcgg cgcagttcac ccgcaatact cgtttaggta ttcctttggc atcggctgcg   180
atggacacgg ttactgaggc gcgcatggct attgccatgg cacgccaggg tggcattggt   240
gtcttgcacc gcaacttgtc ctcgcaagag caggcggagc aggtcgaaat cgtcaagcgc   300
atgaccgaaa atcgtgtttc taccggtgga gatgacccaa ataaggttgc attgcatggc   360
ttgacgtttg atgacgtgct gctgctacct gccgaatcca atgttgttcc gtcggaagta   420
gacacttcgg cgcagttcac ccgcaatact cgtttaggta ttcctttggc atcggctgcg   480
atggacacgg ttactgaggc gcgcatggct attgccatgg cacgccaggg tggcattggt   540
gtcttgcacc gcaacttgtc ctcgcaagag caggcggagc aggtcgaaat cgtcaagcgc   600
tctgagtccg gcatggtcac cgaccctgtg accgcgaatc cagacatgac tatccaggaa   660
gttgatgacc tgtgtgcacg cttccgcatc tctggtcttc ctgtggtcaa cgaagacggc   720
accttgttgg gcatttgcac caaccgcgat atgcgctttg agcgcgacta ttcccgcaag   780

```
gtttctgaca tcatgaccgc tatgccgctg gttgtggcaa agaaggcgt cagcaaggaa      840
gaagccctgg atctgctgtc gacgaacaag gtagaaaagc tacctatcgt tgataaaaac    900
aacaagctgg tcggtctgat taccgttaaa gactttgtta agaccgaaca gttcccgaat    960
tcctccaagg atgcttcggg ccgcttgcta gtagcagcag gtattggtac cggcgaggag    1020
tcttatgagc gtgcaggctt gcttgtcgat gccggcgtgg acgttctcat tgtcgactcc    1080
gcacacgcgc acaataaccg cgtgctggaa atggtctcgc gcgtcaagaa tgacttcggc    1140
tccaagattg atgttgtcgg cggcaacctg gcaacacgct cggcagcaaa ggcgatgatt    1200
gaggctggcg cagacgccat caaggtgggt attggtcctg gttctatctg caccacccgt    1260
gtggttgctg gtgttggtgc accacagatt accgcgatca tggaagcagc taccgtggct    1320
tctgctgcgg gcgtgccttt gattgcagac ggcggcatgc agtactccgg tgacgttgct    1380
aaggctttgg ctgctggcgc ggactcggtc atgctgggct cgatgttcgc aggcaccctg    1440
gaggctcctg gtgacatcgt gattgtcggc ggcaagcagt acaagcgcta ccgcggcatg    1500
ggttcgatgg gcgctatgca aggccgtggc ctctccggcg agaagcgttc ttactccaag    1560
gaccgctact tccaggcaga tgtgcgcagc gaagataagc tggttccaga aggcgtggaa    1620
ggcaaggttc cttaccgcgg cgaaattggt cagattaccc accagattgt gggcggtttg    1680
cgcgcggcaa tgggctacac tggctccgct actattgaag agctgaagac caagcagttc    1740
gtgcgtatta ccactgctgg cttggctgag tcgcacccgc accacctgca gcaaactgta    1800
gaagctccga actaccgtta a                                              1821
```

```
<210> SEQ ID NO 11
<211> LENGTH: 29
<212> TYPE: DNA
<213> ORGANISM: Artificial Sequence
<220> FEATURE:
<223> OTHER INFORMATION: guaB alt-1

<400> SEQUENCE: 11
gctctagact acgacaacac ggtgcctaa                                      29

<210> SEQ ID NO 12
<211> LENGTH: 37
<212> TYPE: DNA
<213> ORGANISM: Artificial Sequence
<220> FEATURE:
<223> OTHER INFORMATION: guaB alt-2

<400> SEQUENCE: 12
cacgattttc ggtcaatacg ggtcttctcc ttcgcac                             37

<210> SEQ ID NO 13
<211> LENGTH: 36
<212> TYPE: DNA
<213> ORGANISM: Artificial Sequence
<220> FEATURE:
<223> OTHER INFORMATION: guaB alt-3

<400> SEQUENCE: 13
aggagaagac ccgtattgac cgaaaatcgt gtttct                              36

<210> SEQ ID NO 14
<211> LENGTH: 29
<212> TYPE: DNA
<213> ORGANISM: Artificial Sequence
<220> FEATURE:
```

<223> OTHER INFORMATION: guaB alt-4

<400> SEQUENCE: 14
gctctagaat cgacaagcaa gcctgcacg                                29

<210> SEQ ID NO 15
<211> LENGTH: 29
<212> TYPE: DNA
<213> ORGANISM: Artificial Sequence
<220> FEATURE:
<223> OTHER INFORMATION: purA promoter F

<400> SEQUENCE: 15
ggggtaccgg caaaattgcc gccgcagct                                29

<210> SEQ ID NO 16
<211> LENGTH: 29
<212> TYPE: DNA
<213> ORGANISM: Artificial Sequence
<220> FEATURE:
<223> OTHER INFORMATION: purA promoter R

<400> SEQUENCE: 16
gggatatcgg ttattcactt cctagattt                                29

<210> SEQ ID NO 17
<211> LENGTH: 21
<212> TYPE: DNA
<213> ORGANISM: Artificial Sequence
<220> FEATURE:
<223> OTHER INFORMATION: purA lib.R

<400> SEQUENCE: 17
ttatttgtag agctcatcca t                                        21

<210> SEQ ID NO 18
<211> LENGTH: 27
<212> TYPE: DNA
<213> ORGANISM: Artificial Sequence
<220> FEATURE:
<223> OTHER INFORMATION: purA promoter F for cloning PDZ

<400> SEQUENCE: 18
gctctagaac ggtcacgcgc aaatcag                                  27

<210> SEQ ID NO 19
<211> LENGTH: 36
<212> TYPE: DNA
<213> ORGANISM: Artificial Sequence
<220> FEATURE:
<223> OTHER INFORMATION: purA c143t-1R

<400> SEQUENCE: 19
ctacctttat cgccaatgat aatgtattta gccatg                        36

<210> SEQ ID NO 20
<211> LENGTH: 35
<212> TYPE: DNA
<213> ORGANISM: Artificial Sequence
<220> FEATURE:
<223> OTHER INFORMATION: purA c143t-2F

<400> SEQUENCE: 20
ctaaatacat tatcattggc gataaaggta gagtt                         35

```
<210> SEQ ID NO 21
<211> LENGTH: 28
<212> TYPE: DNA
<213> ORGANISM: Artificial Sequence
<220> FEATURE:
<223> OTHER INFORMATION: purA promoter R for cloning PDZ

<400> SEQUENCE: 21
gctctagatc gtaggcgacg caaatagg                                          28

<210> SEQ ID NO 22
<211> LENGTH: 24
<212> TYPE: DNA
<213> ORGANISM: Artificial Sequence
<220> FEATURE:
<223> OTHER INFORMATION: purA a189t-1R

<400> SEQUENCE: 22
ggttattcac tacctagatt taag                                              24

<210> SEQ ID NO 23
<211> LENGTH: 23
<212> TYPE: DNA
<213> ORGANISM: Artificial Sequence
<220> FEATURE:
<223> OTHER INFORMATION: purA a189t-2F

<400> SEQUENCE: 23
ttaaatctag gtagtgaata acc                                               23

<210> SEQ ID NO 24
<211> LENGTH: 38
<212> TYPE: DNA
<213> ORGANISM: Artificial Sequence
<220> FEATURE:
<223> OTHER INFORMATION: Site-directed mutagenesis F

<400> SEQUENCE: 24
tagccttaaa tctaggtagt gaataaccat ggcagcta                               38

<210> SEQ ID NO 25
<211> LENGTH: 38
<212> TYPE: DNA
<213> ORGANISM: Artificial Sequence
<220> FEATURE:
<223> OTHER INFORMATION: Site-directed mutagenesis R

<400> SEQUENCE: 25
tagctgccat ggttattcac tacctagatt taaggcta                               38
```

PROMOTER AND METHOD FOR PRODUCING PURINE NUCLEOTIDE USING THE SAME

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_452USPC_SEQUENCE_LISTING.txt. The text file is 9.7 KB, was created on Aug. 20, 2019, and is being submitted electronically via EFS-Web.

BACKGROUND

Technical Field

The present disclosure relates to a polynucleotide having an activity of a promoter, a composition for gene expression containing the polynucleotide, a microorganism containing the gene, a method for preparing purine nucleotides using the microorganism, and a use of the polynucleotide.

Description of the Related Art

5'-Inosine monophosphate (hereinafter, IMP), a nucleic acid-based material, is an intermediate of the nucleic acid biosynthetic metabolic system used in various fields (e.g., medicines, various medical applications, etc.). In addition, IMP is a material widely used as a food seasoning additive or food along with 5'-guanine monophosphate (hereinafter, GMP). It is known that IMP itself produces a beef flavor and enhances the flavor of monosodium glutamic acid (MSG) like GMP, and thus it has been highlighted as a taste-based nucleic acid-based seasoning.

Methods of preparing IMP may include a method of enzymatically degrading ribonucleic acid extracted from yeast cells, a method of chemically phosphorylating inosine produced by fermentation (*Agri. Biol. Chem.*, 36, 1511 (1972), etc.), a method of culturing a microorganism that directly produces IMP and recovering IMP from the cultured medium, etc. Among these methods, the most widely used method is that of using a microorganism capable of directly producing IMP.

Additionally, the method of preparing GMP may include a method of converting xanthosine 5'-monophosphate (hereinafter, XMP) produced by microbial fermentation into GMP using a coryneform microorganism and a method of converting XMP produced by microbial fermentation into GMP using *Escherichia coli*. Among the above methods, when GMP is produced by a method where XMP is produced first and then converted into GMP, the productivity of XMP (i.e., a precursor of the conversion reaction during the microbial fermentation) must be enhanced, and additionally, the GMP already produced during the entire process of the conversion reaction as well as the produced XMP must be protected from being lost.

Meanwhile, since enzymes in nature do not always exhibit optimal properties in terms of activity, stability, substrate specificity to optical isomers, etc., required in industrial applications, various attempts have been made to improve enzymes to improve the desired use by modification of their amino acid sequences. Among these, rational design and site-directed mutagenesis of enzymes have been applied to improve enzyme functions in some cases; however, these methods have disadvantages in that information on the structure of the target enzyme is not sufficient or the structure-function correlation is not clear, and thus they cannot be effectively applied. In this case, it has been reported that the activity of an enzyme can be enhanced by improving the enzyme through a directed evolution method, in which enzymes of desired traits are screened from a library of enzyme variants constructed through random modification of enzyme genes.

DISCLOSURE

Technical Problem

The inventors of the present disclosure have performed extensive research for high-yield production of purine nucleotides through microbial fermentation. As a result, they have discovered promoters which are more effective for higher productivity of purine nucleotides, thereby completing the present disclosure.

Technical Solution

An object of the present disclosure is to provide a polynucleotide having an activity of a promoter.

Another object of the present disclosure is to provide a composition for gene expression containing the polynucleotide.

Still another object of the present disclosure is to provide a vector containing the polynucleotide and a gene encoding a target protein.

Still another object of the present disclosure is to provide a microorganism of the genus *Corynebacterium* containing the vector.

Still another object of the present disclosure is to provide a microorganism of the genus *Corynebacterium* containing the polynucleotide and a gene encoding a target protein.

Still another object of the present disclosure is to provide a method for preparing purine nucleotides, which includes culturing the microorganism of the genus *Corynebacterium* in a medium.

Still another object of the present disclosure is to provide a use of the polynucleotide for increasing the expression of a target protein.

Advantageous Effects

When a microorganism of the genus *Corynebacterium* is cultured using a polynucleotide having a novel promoter activity of the present disclosure, it is possible to produce purine nucleotides in high yield. Additionally, the prepared purine nucleotides can be applied not only to animal feeds or animal feed additives but also to various products such as human foods, food additives, medicines, etc.

Best Mode

The present disclosure is described in detail as follows. Meanwhile, respective descriptions and embodiments disclosed in the present disclosure may also be applied to other descriptions and embodiments. That is, all combinations of various elements disclosed in the present disclosure belong to the scope of the present disclosure. Further, the scope of the present disclosure is not limited by the specific description below.

To achieve the above objects, an aspect of the present disclosure provides a polynucleotide of SEQ ID NO: 1 having a promoter activity, in which the polynucleotide sequence includes at least one nucleotide substitution therein. Specifically, the present disclosure provides a polynucleotide of SEQ ID NO: 1 having a promoter activity in which the polynucleotide sequence includes at least one nucleotide substitution therein, and the polynucleotide substitution is at least one selected from the group consisting of a substitution of the $143^{rd}$ nucleotide and a substitution of the $189^{th}$ nucleotide.

Another aspect of the present disclosure provides a polynucleotide having an activity of a promoter, in which, in the polynucleotide sequence of SEQ ID NO: 1, i) the $143^{rd}$ nucleotide is substituted with thymine (T); ii) the $189^{th}$ nucleotide is substituted with thymine (T); or iii) the $143^{rd}$ nucleotide is substituted with thymine (T) and the $189^{th}$ nucleotide is substituted with thymine (T).

As used herein, the term "polynucleotide" refers to a DNA strand having more than a certain length as a nucleotide polymer, which is a long chain of nucleotide monomers connected by covalent bonds.

As used herein, the term "polynucleotide having a promoter activity" refers to a DNA region present in the vicinity of a region, which is involved in the transcription of a target gene including an RNA polymerase, an enhancer, etc., for the expression of the target gene to be connected downstream thereof. For the purpose of the present disclosure, the polynucleotide may be used as an attenuated promoter for general use, for example, as a promoter that can attenuate the expression of adenylosuccinate synthetase. Additionally, the polynucleotide refers to a polynucleotide involved in the production or increase of purine nucleotides, but the polynucleotide is not limited thereto.

As used herein, SEQ ID NO: 1 refers to a polynucleotide sequence having a promoter activity. The polynucleotide sequence of SEQ ID NO: 1 may be obtained from NCBI GenBank, which is a known database. In an embodiment, the polynucleotide sequence of SEQ ID NO: 1 may be derived from a microorganism of the genus *Corynebacterium*, but the microorganism is not limited thereto.

Additionally, the polynucleotide may be one in which, in the sequence of SEQ ID NO: 1, the $143^{rd}$ nucleotide and/or the $189^{th}$ nucleotide are substituted with a different nucleotide. Such a polynucleotide may refer to the nucleotide sequence of SEQ ID NO: 1 and/or a nucleotide sequence having at least 80%, 85%, 90%, 95%, 96%, 97%, 98%, or 99% or more homology or identity to the nucleotide sequence of SEQ ID NO: 1, in which the $143^{rd}$ nucleotide and/or the $189^{th}$ nucleotide are substituted with a different nucleotide. The nucleotide sequence having homology or identity may be those in the above range, excluding a sequence having 100% identity, or may be a sequence having less than 100% identity.

In an embodiment, the polynucleotide sequence of the present disclosure may be one in which, in the polynucleotide sequence of SEQ ID NO: 1, i) the $143^{rd}$ nucleotide is substituted with thymine (T); ii) the $189^{th}$ nucleotide is substituted with thymine (T); or iii) the $143^{rd}$ nucleotide is substituted with thymine (T) and the $189^{th}$ nucleotide is substituted with thymine (T), but the polynucleotide sequence is not limited thereto. Specifically, the polynucleotide sequence of the present disclosure may include the nucleotide sequence of SEQ ID NO: 2, SEQ ID NO: 3, or SEQ ID NO: 4, but the polynucleotide sequence is not limited thereto. More specifically, in the polynucleotide sequence of the present disclosure, the polynucleotide in which the $143^{rd}$ nucleotide is substituted with thymine (T) may consist of the nucleotide sequence of SEQ ID NO: 2; the polynucleotide in which the $189^{th}$ nucleotide is substituted with thymine (T) may consist of the nucleotide sequence of SEQ ID NO: 3; or the polynucleotide in which the $143^{rd}$ nucleotide is substituted with thymine (T) and the $189^{th}$ nucleotide is substituted with thymine (T) may consist of the nucleotide sequence of SEQ ID NO: 4, but the polynucleotide sequence of the present disclosure is not limited thereto. The polynucleotide may be one which has at least 80%, 85%, 90%, 95%, 96%, 97%, 98%, or 99% or more homology or identity to the nucleotide sequence of SEQ ID NO: 2, SEQ ID NO: 3, or SEQ ID NO: 4. The polynucleotide sequence having homology or identity may be those in the above range, excluding a sequence having 100% identity, or may be a sequence having less than 100% identity.

Additionally, it is apparent that any polynucleotide having a polynucleotide sequence with deletion, modification, substitution, or addition in part of the sequence may also be used in the present disclosure, as long as the polynucleotide has an activity equivalent or corresponding to a polynucleotide consisting of a nucleotide sequence of the corresponding SEQ ID NO, even if it is described as "polynucleotide having a nucleotide sequence of a particular SEQ ID NO" in the present disclosure. For example, as long as the polynucleotide variant has activity identical or corresponding to that of the polypeptide, it does not exclude an addition of a nonsense sequence upstream or downstream of the corresponding SEQ ID NO, naturally occurring mutation, or silent mutation, in addition to the particular modification at position 143 or 189 providing a particular activity therefrom, and such a sequence addition or mutation also falls within the scope of the present disclosure.

Homology and identity refer to a degree of relatedness between two given nucleotide sequences and may be expressed as a percentage.

The terms "homology" and "identity" may often be used interchangeably with each other.

Sequence homology or identity of a conserved polynucleotide may be determined by a standard alignment algorithm and default gap penalties established by a program to be used may be used in combination. Substantially, homologous or identical sequences may hybridize under moderately or highly stringent conditions along their entire sequence or at least about 50%, about 60%, about 70%, about 80%, or about 90% of the entire length. With regard to the polynucleotides to be hybridized, polynucleotides including a degenerate codon instead of a codon may also be considered.

Whether any two polynucleotide sequences have homology, similarity, or identity may be determined by, for example, a known computer algorithm such as the "FASTA" program using default parameters as in Pearson et al. (1988) (*Proc. Natl. Acad. Sci. USA* 85]: 2444). Alternatively, they may be determined using the Needleman-Wunsch algorithm (Needleman and Wunsch, 1970, *J. Mol. Biol.* 48: 443 to 453) as performed in the Needleman program of the EMBOSS package (EMBOSS: The European Molecular Biology Open Software Suite, Rice et al., 2000, *Trends Genet.* 16: 276 to 277) (version 5.0.0 or later) (including GCG program package (Devereux, J., et al., *Nucleic Acids Research* 12: 387 (1984)), BLASTP, BLASTN, FASTA (Atschul, [S.] [F.] et al., *J Molec Biol* 215]: 403 (1990); Guide to Huge Computers, Martin J. Bishop, [ED.,] Academic Press, San Diego, 1994, and [CARILLO ETA/.] (1988) *SIAM J Applied Math* 48: 1073). For example, homology, similarity, or identity may be determined using BLAST or ClustalW of the National Center for Biotechnology Information.

Homology, similarity, or identity of polynucleotides may be determined by comparing sequence information using a GAP computer program (e.g., Needleman et al. (1970), *J Mol Biol* 48: 443) as disclosed in Smith and Waterman, *Adv. Appl. Math* (1981) 2:482. Briefly, the GAP program defines similarity as the number of aligned symbols (i.e., nucleotides or amino acids) which are similar, divided by the total number of symbols in the shorter of the two sequences. The default parameters for the GAP program may include: (1) a unary comparison matrix (containing a value of 1 for identities and 0 for non-identities) and the weighted comparison matrix (or EDNAFULL (EMBOSS version of NCBI NUC4.4) substitution matrix) of Gribskov et al. (1986) *Nucl. Acids Res.* 14: 6745, as disclosed by Schwartz and Dayhoff, eds., Atlas Of Protein Sequence And Structure, National Biomedical Research Foundation, pp. 353 to 358 (1979); (2) a penalty of 3.0 for each gap and an additional 0.10 penalty for each symbol in each gap (or gap open penalty 10, gap extension penalty 0.5); and (3) no penalty for end gaps. Therefore, the term "homology" or "identity", as used herein, represents relevance between sequences.

Additionally, due to codon degeneracy or by considering the codons preferred in a bioorganism where the polynucleotide is to be expressed, various modifications may be performed in the coding region of the polynucleotide within the scope that does not alter the polynucleotide sequence. Any polynucleotide sequence in which the $143^{rd}$ nucleotide and/or the $189^{th}$ nucleotide of the nucleotide sequence of SEQ ID NO: 1 is substituted with a different nucleotide may be included without limitation. Additionally, any polynucleotide sequence, in which the $143^{rd}$ nucleotide and/or the $189^{th}$ nucleotide of the nucleotide sequence of SEQ ID NO: 1 is substituted with a different nucleotide, that can be hybridized under stringent conditions with any probe that can be prepared from known gene sequences (e.g., complementary sequences to all or part of the above nucleotide sequence) can be included without limitation.

The term "stringent conditions" refers to conditions which enables specific hybridization between polynucleotides. Such conditions are specifically described in references (e.g., J Sambrook et al.). For example, the conditions may include performing hybridization between genes having a high homology, a homology of 40% or higher, specifically 80% or higher, 85% or higher, and 90% or higher, more specifically 95% or higher, even more specifically 97% or higher, and most specifically 99% or higher, while not performing hybridization between genes having a homology of lower than the homologies described above; or performing hybridization once, specifically two or three times, under conventional washing conditions for southern hybridization of 60° C., 1×SSC, and 0.1% SDS, specifically at a salt concentration and temperature corresponding to 60° C., 0.1×SSC, and 0.1% SDS, and more specifically 68° C., 0.1×SSC, and 0.1% SDS.

Hybridization requires that two nucleic acids have complementary sequences, although mismatches between bases may be possible depending on hybridization stringency. The term "complementary" is used to describe the relationship between nucleotide bases that can hybridize to each other. For example, with respect to DNA, adenosine is complementary to thymine and cytosine is complementary to guanine. Accordingly, the present disclosure may also include isolated nucleic acid fragments complementary to the entire sequence as well as to substantially similar nucleic acid sequences.

Specifically, polynucleotides having a homology can be detected at a $T_m$ value of 55° C. using hybridization conditions that include a hybridization step and using the conditions described above. Additionally, the $T_m$ value may be 60° C., 63° C., or 65° C., but the temperature is not limited thereto and may be appropriately adjusted by those skilled in the art according to the intended purpose.

The stringency suitable for the hybridization of polynucleotides depends on the length and degree of complementarity of the polynucleotides, and the related variables are well known in the art (see Sambrook et al., supra, 9.50 to 9.51 and 11.7 to 11.8).

Still another aspect of the present disclosure provides a composition for gene expression containing the polynucleotide.

The composition for gene expression refers to a composition capable of expressing a gene which can be expressed by the promoter of the present disclosure. For example, the composition for gene expression may include a polynucleotide having a novel promoter activity, and may further include any constitution capable of operating the polynucleotide as a promoter without limitation. In the composition for gene expression of the present disclosure, the polynucleotide may be in a form included in a vector so as to express a gene operably linked in a host cell into which the polynucleotide is introduced.

Still another aspect of the present disclosure provides a polynucleotide having the promoter activity, or a vector which includes the polynucleotide and a gene encoding a target protein. Specifically, the target protein may be adenylosuccinate synthetase but is not limited thereto.

As used herein, the term "vector" refers to a DNA construct containing the nucleotide sequence encoding of a target polynucleotide, which is operably linked to an appropriate control sequence such that the target polypeptide is expressed in an appropriate host. The control sequence may include a promoter to initiate transcription, any operator sequence to control such transcription, a sequence encoding an appropriate ribosome-binding site on mRNA, and a sequence to control termination of transcription and translation. Upon transformation into an appropriate host cell, the vector may replicate or function independently of the host genome, or may integrate into the genome itself.

The vector used in the present disclosure may not be particularly limited as long as the vector is replicable in a host cell, and any vector known in the art may be used. Examples of the vector commonly used may include natural or recombinant plasmids, cosmids, viruses, and bacteriophages. For example, as a phage vector or cosmid vector, pWE15, M13, MBL3, MBL4, IXII, ASHII, APII, t10, t11, Charon4A, Charon21A, etc., may be used, and as a plasmid vector, those based on pBR, pUC, pBluescriptII, pGEM, pTZ, pCL, pET, etc., may be used. Specifically, pDZ, pACYC177, pACYC184, pCL, pECCG117, pUC19, pBR322, pMW118, pCC1BAC vector, etc., may be used.

In an embodiment, the target polynucleotide may be inserted into the chromosome through a vector for chromosomal insertion. The insertion of the polynucleotide into the chromosome may be performed using any method known in the art (e.g., by homologous recombination), but the method is not limited thereto. A selection marker for confirming the insertion of the vector into the chromosome may be further included. The selection marker was used for selection of cells transformed with the vector (i.e., for confirmation of presence of the insertion of the target nucleic acid molecule), and markers capable of providing selectable phenotypes (e.g., drug resistance, auxotrophy, resistance to cytotoxic agents, and expression of surface polypeptides) may be used. Under the circumstances where selective agents are treated, only those cells capable of expressing the selection markers can survive or express other phenotypic traits, and thus the transformed cells can be selected.

Still another aspect of the present disclosure provides a microorganism of the genus *Corynebacterium* including a vector, in which the vector includes a polynucleotide having a promoter activity of the present disclosure and a gene encoding a target protein.

Additionally, still another aspect of the present disclosure provides a microorganism of the genus *Corynebacterium*, which includes a polynucleotide having a promoter activity of the present disclosure and a gene encoding a target protein.

Specifically the microorganism may be a microorganism which is prepared by the transformation via the vector which includes the polynucleotide having a promoter activity and the gene encoding a target protein; or a microorganism which includes the polynucleotide having a promoter activity and the gene encoding a target protein, but the microorganism is not limited thereto.

As used herein, the term "transformation" refers to a process of introducing a vector which includes a polynucleotide encoding a target protein into a host cell such that the protein encoded by the polynucleotide can be expressed in the host cell. It does not matter whether the transformed polynucleotide is inserted into the chromosome of the host cell and located thereon or located outside of the chromosome, as long as the transformed polynucleotide can be expressed in the host cell. Additionally, the polynucleotide includes DNA or RNA encoding the target protein. The polynucleotide may be introduced in any form, as long as the polynucleotide can be introduced into the host cell and expressed therein. For example, the polynucleotide may be introduced into the host cell in the form of an expression cassette, which is a gene construct including all elements required for its autonomous expression. The expression cassette may include a promoter, a transcription termination signal, a ribosome binding site, and a translation termination signal that may be operably linked to the polynucleotide. The expression cassette may be the form of a self-replicable expression vector. Additionally, the polynucleotide may be introduced into the host cell as is to be operably linked to the sequence required for expression in the host cell, but the polynucleotide is not limited thereto.

Additionally, the term "operably linked" refers to a functional linkage between the gene sequence and a promoter sequence which initiates and mediates transcription of the polynucleotide having a promoter activity of the present disclosure.

As used herein, the term "microorganism including a polynucleotide and a target protein" refers to a microorganism in which the expression of a target protein is controlled by the polynucleotide. The microorganism may be a microorganism capable of producing purine nucleotides, a microorganism which naturally has a weak ability to produce purine nucleotides, or a microorganism provided with an ability to produce purine nucleotides in which its parent strain has no ability to produce purine nucleotides. Specifically, the microorganism may be a microorganism in which the activity of adenylosuccinate synthetase, for example, a microorganism including a polynucleotide in which, in the nucleotide sequence of SEQ ID NO: 1, the 143$^{rd}$ nucleotide and/or the 189$^{th}$ nucleotide is substituted with a different nucleotide, but the microorganism is not limited thereto. More specifically, the microorganism may be a microorganism including a polynucleotide having a promoter activity, in which at least one nucleotide in the polynucleotide sequence of SEQ ID NO: 1 is substituted. The polynucleotide substitution may include a substitution of the 143$^{rd}$ nucleotide with thymine (T) and/or a substitution of the 143$^{rd}$ nucleotide with thymine (T).

For the host cell or microorganism, for the purpose of the present disclure, any host cell or microorganism which is able to produce purine nucleotides by including the polynucleotide and a target protein may belong to the scope of the present disclosure.

In the present disclosure, the microorganism capable of producing purine nucleotides may be used interchangeably with a microorganism producing purine nucleotides and a microorganism having the ability of producing purine nucleotides.

For the purpose of the present disclosure, the term "purine nucleotide" refers to a nucleotide having a purine-based structure, for example, IMP, XMP, or GMP, but the purine nucleotide is not limited thereto.

Specifically, the term "5'-inosine monophosphate (IMP)" is a nucleic acid material consisting of Formula 1 below.

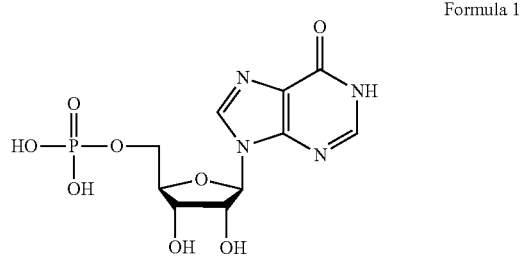

Formula 1

IMP is also referred to by its IUPAC names, 5'-inosine monophosphate or 5'-inosine acid, and IMP is widely used in foods as a flavor enhancer along with XMP or GMP.

The term "5'-guanine monophosphate (GMP)" refers to a nucleic acid material consisting of Formula 2 below.

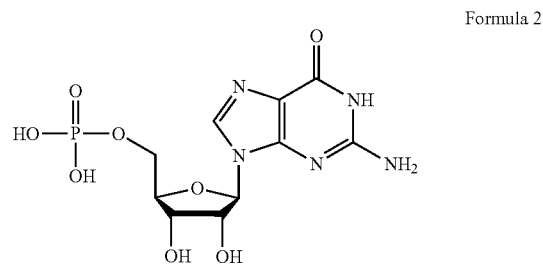

Formula 2

GMP is also referred to by its IUPAC names, [(2R,3S,4R,5R)-5-(2-Amino-6-oxo-1,6-dihydro-9H-purin-9-yl)-3,4-dihydroxytetrahydro-2-furanyl]methyl dihydrogen phosphate, 5'-guanidylic acid, 5'-guanylic, or guanylic acid.

GMP is in the form of a salt and is widely used as a food additive, such as sodium guanylate, dipotassium guanylate, and calcium guanylate. GMP has a synergistic effect to enhance tastes when it is used as an additive together with IMP. GMP may be prepared by conversion from XMP, but the method of GMP preparation is not limited thereto. As confirmed in an embodiment of the present disclosure, the promoter of the present disclosure can increase the production of XMP, and GMP can also be converted from XMP thereby increasing the amount of GMP production. Therefore, it is apparent that GMP also belongs to the scope of the present disclosure.

As used herein, the term "5'-xanthosine monophosphate (XMP)" is an intermediate material of purine metabolism, consisting of Formula 3 below.

XMP is also referred to by its IUPAC names, 5'-inosine monophosphate or 5'-xanthylic acid. XMP may be formed from IMP through the action of dehydrogenase, or may be converted to GMP through the action of GMP synthase. Additionally, XMP may be formed from XTP by deoxyribonucleoside triphosphate pyrophosphohydrolase, which is an enzyme including the XTPase activity.

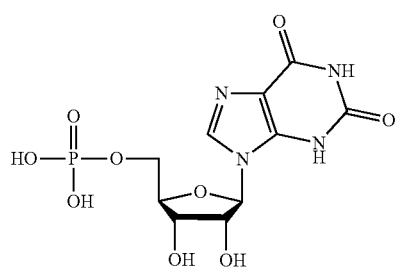

Formula 3

As used herein, the term "microorganism producing purine nucleotides" includes both a wild-type microorganism and microorganisms in which a natural or artificial genetic modification has occurred, and the microorganism may be a microorganism in which a particular mechanism is enhanced or weakened due to reasons such as insertion of an exogenous gene, enhancement or inactivation of activity of an endogenous gene, etc. The microorganism may be a microorganism in which a genetic modification has occurred or an activity thereof is enhanced for the intended production of purine nucleotides. For the purpose of the present disclosure, the microorganism producing purine nucleotides is characterized in that it has increased productivity of the desired purine nucleotides by containing the polynucleotide, and specifically, the microorganism may be a microorganism of the genus *Corynebacterium*. Specifically, the microorganism producing purine nucleotides or microorganism capable of producing purine nucleotides may be a microorganism in which some of the genes involved in the purine nucleotide biosynthesis pathway are enhanced or weakened, or some of the gene involved in the purine nucleotide degradation pathway are enhanced or weakened, or part of the gene(s) involved in the purine nucleotide degradation pathway is enhanced or weakened. For example, the microorganism may be a microorganism in which the expression of purF encoding phosphoribosylpyrophosphate amidotransferase or the expression of purA is enhanced. Additionally, according to the purine nucleotide, the expression of guaB, which is a gene encoding inosine-5'-monophosphate dehydrogenase, may be controlled. Specifically, when the purine nucleotide is IMP, the expression of guaB may be weakened, whereas when the purine nucleotide is XMP or GMP, the expression of guaB may be enhanced.

As used herein, the term "microorganism of the genus *Corynebacterium* producing 5'-purine nucleotides" refers to a microorganism of the genus *Corynebacterium* which has the ability to produce purine nucleotides naturally or by modification. Specifically, as used herein, the microorganism of the genus *Corynebacterium* having the ability to produce purine nucleotides may be a microorganism of the genus *Corynebacterium* which has an improved ability of producing purine nucleotides due to inclusion of the polynucleotide having a promoter activity of the present disclosure, or due to transformation by a vector including the polynucleotide and a gene encoding a target protein.

The "microorganism of the genus *Corynebacterium* having an improved ability of producing purine nucleotides" refers to a microorganism having an improved ability of producing purine nucleotides, compared to its parent strain before transformation or an unmodified microorganism. The "unmodified microorganism" refers to a wild-type strain itself, a microorganism that does not include the modified protein producing purine nucleotides, or a microorganism that is not transformed with the vector including the polynucleotide and a gene encoding a target protein.

As used herein, the "microorganism of the genus *Corynebacterium*" may be specifically *Corynebacterium glutamicum*, *Corynebacterium ammoniagenes*, *Brevibacterium lactofermentum*, *Brevibacterium flavum*, *Corynebacterium thermoaminogenes*, *Corynebacterium efficiens*, *Corynebacterium stationis*, etc., but the microorganism of the genus *Corynebacterium* is not necessarily limited thereto.

Still another aspect of the present disclosure provides a method for preparing a target material which includes culturing the microorganism of the genus *Corynebacterium* in a medium. In an embodiment, the method of the present disclosure may further include a step of recovering the target material form the microorganism or cultured medium after the step of culturing. Specifically, the target material may be purine nucleotides but is not limited thereto.

In the above method, culturing the microorganism may be performed by a known batch culture, continuous culture, fed-batch culture, etc., but the method of culture is not particularly limited thereto. In particular, the culture conditions may not be particularly limited, but an appropriate pH (e.g., pH 5 to pH 9, specifically pH 6 to pH 8, and most specifically pH 6.8) may be adjusted using a basic compound (e.g., sodium hydroxide, potassium hydroxide, or ammonia) or an acidic compound (e.g., phosphoric acid or sulfuric acid), and an aerobic condition may be maintained by adding oxygen or an oxygen-containing gas mixture to the culture. The culture temperature may be maintained at 20° C. to 45° C., and specifically at 25° C. to 40° C., and the cultivation may be performed for about 10 hours to about 160 hours, but the conditions are not limited thereto. The purine nucleotides produced by the culture may be secreted into the medium or may remain within the cells.

Furthermore, in the culture medium to be used, as a carbon source, saccharides and carbohydrates (e.g., glucose, sucrose, lactose, fructose, maltose, molasses, starch, and cellulose), oils and fats (e.g., soybean oil, sunflower seed oil, peanut oil, and coconut oil), fatty acids (e.g., palmitic acid, stearic acid, and linoleic acid), alcohols (e.g., glycerol and ethanol), organic acids (e.g., acetic acid), etc., may be used alone or in combination, but the carbon source is not limited thereto. As a nitrogen source, a nitrogen-containing organic compound (e.g., peptone, yeast extract, meat extract, malt extract, corn steep liquor, soybean flour, and urea) or an inorganic compound (e.g., ammonium sulfate, ammonium chloride, ammonium phosphate, ammonium carbonate, and ammonium nitrate), etc., may be used alone or in combination, but the nitrogen source is not limited thereto. As a phosphorus source, potassium dihydrogen phosphate, dipotassium hydrogen phosphate, a sodium-containing salt corresponding thereto, etc., may be used alone or in combination, but the phosphorus source is not limited thereto.

Additionally, the medium may also include essential growth-promoting materials such as other metal salts (e.g., magnesium sulfate or iron sulfate), amino acids, and vitamins.

A method of recovering purine nucleotides produced in the culture step of the present disclosure is to collect the target purine nucleotides from the culture using an appropriate method known in the art according to the culture method. For example, centrifugation, filtration, anion exchange chromatography, crystallization, HPLC, etc., may be used, and the target purine nucleotides may be recovered from the medium or microorganism using an appropriate method known in the art.

Additionally, the recovering step may include a purification process. The purification process may be performed using an appropriate method known in the art. Therefore, the recovered purine nucleotides may be in a purified form or a microbial fermentation liquid including purine nucleotides (Introduction to Biotechnology and Genetic Engineering, A. J. Nair, 2008).

Additionally, for the purpose of the present disclosure, in a case where a microorganism includes a polynucleotide having the above-described promoter activity, the microorganism is characterized in that the amount of a target material is increased. In particular, while a wild-type strain of the genus *Corynebacterium* cannot produce purine nucleotides at all, or produces only a trace amount even if it is possible, the microorganism of the present disclosure, by including a polynucleotide having the promoter activity, can increase the amount of the production of purine nucleotides.

Still another aspect of the present disclosure provides a use of the polynucleotide for increasing the expression of a target protein.

DETAILED DESCRIPTION

Hereinafter, the present disclosure will be described in detail through exemplary embodiments. However, it will be apparent to those skilled in the art to which the present disclosure belongs that these exemplary embodiments are provided for the purpose of illustration only and are not intended to limit the scope of the present disclosure.

Example 1: Preparation of Wild-Type Based IMP-Producing Strain

A wild-type strain of the genus *Corynebacterium* cannot produce IMP at all or produce only a trace amount even if it is possible. Therefore, an IMP-producing strain was prepared based on the wild-type strain of *Corynebacterium stationis* ATCC6872. More specifically, a strain was prepared in which the activity of purF gene, which encodes phosphoribosylpyrophosphate amidotransferase, is enhanced and the activity of guaB, which encodes IMP is weakened.

Example 1-1: Preparation of purF-Enhanced Strain

To prepare a strain in which the start codon of purF gene is modified, an insertion vector containing the purF gene was first prepared. To clone the purF gene into an insertion vector, specifically, PCR was performed using the genomic DNA of *Corynebacterium* stationis ATCC6872 as a template and the primer sets of SEQ ID NOS: 6 and 7 and SEQ ID NOS: 8 and 9 for 30 cycles of denaturation at 94° C. for 30 sec, annealing at 55° C. for 30 sec, and extension at 72° C. for 2 min. PCR was performed again using two DNA fragments obtained by the above PCR as a template and the primer set of SEQ ID NOS: 6 and 9 for 30 cycles of denaturation at 94° C. for 30 sec, annealing at 55° C. for 30 sec, and extension at 72° C. for 2 min to obtain DNA fragments. The obtained DNA fragments were digested with restriction enzyme XbaI and cloned into the pDZ vector (Korean Patent No. 10-0924065 and International Patent Publication No. WO 2008-033001) digested with the same enzyme. The thus-prepared vector was named as pDZ-purF-g1a.

TABLE 1

| SEQ ID NO | Primer | Sequence (5'-3') |
|---|---|---|
| 6 | purF g1a-1 | GCTCTAGACCACTCTAAGACGCGGCCACC |
| 7 | purF g1a-2 | AAGTAGTGTTCACCATGACGCTGATTCTACTAAGTTT |
| 8 | purF g1a-3 | AGTAGAATCAGCGTCATGGTGAACACTACTTTCCCCAG |
| 9 | purF g1a-4 | GCTCTAGACTGTGCGCCCACGATATCCAG |

The recombinant vector pDZ-purF-g1a was transformed into *Corynebacterium stationis* ATCC6872 by electroporation, and strains in which the vector was inserted into the chromosome by homologous recombination were selected on a medium containing 25 mg/L kanamycin. The selected primary strains were subjected to secondary crossover, and these selected strains were subjected to sequencing, and thereby the final strain into which the modification was introduced was selected. The strain was named as 6872-purF(g1a) strain.

Example 1-2: Preparation of guaB-Weakened Strain

To prepare a strain in which the start codon of guaB gene is modified, an insertion vector containing the guaB gene was prepared. To clone the guaB gene into the insertion vector, specifically, PCR was performed using the genomic DNA of *Corynebacterium stationis* ATCC6872 as a template and the primer sets of SEQ ID NOS: 11 and 12 and SEQ ID NOS: 13 and 14. PCR was performed again using the PCR products obtained by the above PCR as a template and the primer set of SEQ ID NOS: 11 and 14 and the obtained DNA fragments were cloned as in Example 1-1. The thus-prepared vector was named as pDZ-guaB-alt. The vector was introduced into the 6872-purF(g1a) in the same manner and the strain in which the above modification was introduced was finally selected. The finally selected strain producing IMP was named as CJI2330.

TABLE 2

| SEQ ID NO | Primer | Sequence (5'-3') |
| --- | --- | --- |
| 11 | guaB alt-1 | GCTCTAGACTACGACAACACGGTGCCTAA |
| 12 | guaB alt-2 | CACGATTTTCGGTCAATACGGGTCTTCTCCTTCGCAC |
| 13 | guaB alt-3 | AGGAGAAGACCCGTATTGACCGAAAATCGTGTTTCT |
| 14 | guaB alt-4 | GCTCTAGAATCGACAAGCAAGCCTGCACG |

Example 1-3: Fermentation Titer Test of CJI2330

After dispensing a seed culture medium (2 mL) into test tubes (diameter: 18 mm), the tubes were autoclaved. Each of ATCC6872 and CJI2330 was inoculated and incubated at 30° C. for 24 hours with shaking and used as a seed culture. A fermentation medium was dispensed (29 mL each) into 250 mL shaking Erlenmeyer flasks and autoclaved at 121° C. for 15 min. The seed culture (2 mL) was inoculated to the medium and cultured for 3 days. Culture conditions were adjusted to 170 rpm, 30° C., and pH 7.5.

After completion of the culture, the amount of IMP production was measured by HPLC (SHIMAZDU LC20A) and the culture results are as in Table 3 below. The following results suggest that CJI2330 has the ability to produce IMP.

TABLE 3

| Strain | IMP (g/L) |
| --- | --- |
| ATCC6872 | 0 |
| CJI2330 | 0.50 |

Seed culture medium: 1% glucose, 1% peptone, 1% meat extract, 1% yeast extract, 0.25% sodium chloride, 100 mg/L adenine, 100 mg/L guanine, pH 7.5

Fermentation medium: 0.1% sodium glutamate, 1% ammonium chloride, 1.2% magnesium sulfate, 0.01% calcium chloride, 20 mg/L iron sulfate, 20 mg/L manganese sulfate, 20 mg/L zinc sulfate, 5 mg/L copper sulfate, 23 mg/L L-cysteine, 24 mg/L alanine, 8 mg/L nicotinic acid, 45 μg/L biotin, 5 mg/L thiamine hydrochloride, 30 mg/L adenine, 1.9% phosphoric acid (85%), 2.55% glucose, 1.45% fructose

Example 2: Discovery of Modification in which purA Promoter Activity is Weakened To weaken the expression of adenylosuccinate synthetase for the improvement of the purine nucleotide-producing ability, a variant library of purA gene encoding adenylosuccinate synthetase was prepared and attempts were made to discover promoter-weakened modification, in which the promoter activity was weakened, which increases the production of purine nucleotides.

Example 2-1: Preparation of Vector Containing purA Promoter

To prepare a variant library of purA promoter, a green fluorescent protein (GFP) expression vector containing the purA promoter of SEQ ID NO: 1 was first prepared. PCR was performed using the genomic DNA of *Corynebacterium stationis* ATCC6872 as a template and a primer set of SEQ ID NO: 15 and SEQ ID NO: 16 for 30 cycles of denaturation at 94° C. for 30 sec, annealing at 55° C. for 30 sec, and extension at 72° C. for 2 min. The obtained DNA fragments were digested with KpnI and EcoRV and cloned into the p117-gfp vector (Korean Patent Application Publication No. 10-0620092), which was already digested with the same restriction enzymes, and the thus-prepared vector was named as p117-PpurA-gfp.

TABLE 4

| SEQ ID NO | Primer | Sequence (5'-3') |
| --- | --- | --- |
| 15 | purA promoter F | GGGGTACCGGCAAAATTGCCGCCGCAGCT |
| 16 | purA promoter R | GGGATATCGGTTATTCACTTCCTAGATTT |
| 17 | purA promoter lib R | TTATTTGTAGAGCTCATCCAT |

Example 2-2: Preparation of Variant Library of purA Promoter

A variant library of purA gene was prepared based on the vector prepared in Example 2-1. The library was prepared using an error-prone PCR kit (Clontech Diversify® PCR Random Mutagenesis Kit). Under conditions where modifications may occur, PCR was performed using a primer set of SEQ ID NOS: 15 and 17. Specifically, under conditions where 2 to 4 modifications may occur per 1,000 bp, pre-heating was performed at 94° C. for 30 seconds, followed by 25 cycles of a process of 94° C. for 30 seconds and 68° C. for 1 minute 30 seconds. A thus-obtained PCR product was subjected to PCR using a megaprimer (500 ng to 125 ng) for 25 cycles of a process of 95° C. for 50 seconds, 60° C. for 50 seconds, and 68° C. for 12 min, treated with DpnI, and transformed into *E. coli* DH5α and spread on an LB solid medium containing kanamycin (25 mg/L). After selecting 20 different kinds of transformed colonies, plasmids were obtained therefrom and subjected to sequencing analysis. As a result, it was confirmed that modifications were introduced at different sites at a frequency of 3.5 modifications/kb. About 10,000 transformed *E. coli* colonies were collected and their plasmids were extracted, and named as "p117-PpurA-gfp-library".

Example 3: Evaluation of Prepared Library and Selection of Variants

Example 3-1: Evaluation of Library

The p117-PpurA-gfp-library prepared in Example 2-2 was transformed into the CJI2330 strain prepared in Example 1 by electroporation, and the strain was spread on a nutrient medium containing 25 mg/L kanamycin to obtain 5,000 colonies into which the modified vector was inserted. The colonies were named as "CJI2330p117-PpurA(mt1)" to "CJI2330p117-PpurA(mt5000)".

Nutrient medium: 1% peptone, 1% meat extract, 0.25% sodium chloride, 1% yeast extract, 2% agar, pH 7.2 Each of the obtained 5,000 colonies was inoculated in 200 µL of an autoclaved seed culture medium, and cultured in a 96-deep-well plate with shaking at 30° C. and 1,200 rpm for 24 hours using a microplate shaker (TAITEC), and used as a seed culture. The autoclaved fermentation medium (290 µL) was dispensed into a 96-deep-well plate, and 20 µL of each of the seed cultures was inoculated thereto and cultured with shaking under the same conditions as above for 72 hours to obtain the cells. Then, the collected cells were washed with 1× phosphate-buffered saline (sodium chloride (80 g), potassium chloride (2 g), sodium phosphate (14.4 g), potassium phosphate (2.4 g), and sterile water (0.8 L)), resuspended in the same buffer, and the fluorescence intensity was measured. The fluorescence intensity was measured by the irradiation of excitation light at 488 nm, and the light emitted therefrom was measured at 511 nm using the microplate reader, and thereby the expression level of the GFP gene was measured. Upon measurement, two mutant colonies were selected (i.e., PpurA(mt3) and PpurA(mt378)) in which the fluorescence intensity was weakened compared to the wild-type gfp.

Example 3-2: Confirmation of Modification in purA Promoter

To confirm the gene modification of the mutant strain, PCR was performed in each of the PpurA(mt3) amd PpurA (mt378) strains using the primer set of SEQ ID NOS: 15 and 17, and the PCR product was subjected to sequencing, thereby confirming the presence of modification in the purA promoter.

Specifically, it was confirmed that the PpurA(mt3) included a polynucleotide sequence in which the $189^{th}$ nucleotide of the polynucleotide sequence of SEQ ID NO: 1 is substituted with thymine (T). Additionally, it was confirmed that the PpurA(mt378) included a polynucleotide sequence in which the $143^{rd}$ nucleotide of the polynucleotide sequence of SEQ ID NO: 1 is substituted with thymine (T). Accordingly, in Examples hereinbelow, attempts were made to confirm whether the above modification can affect the amount of purine nucleotide production in each microorganism of the genus *Corynebacterium*.

Example 4: Confirmation of Ability of IMP Production in IMP-Producing Strain Derived from ATCC6872

An IMP-producing strain derived from ATCC6872 was prepared, and the modification confirmed in Example 3 was introduced into the strain and the ability of producing IMP of the strain was confirmed.

Example 4-1: Selection of IMP-Producing Strain Derived from ATCC6872

To prepare an IMP-producing strain derived from the ATCC6872 strain, the culture of ATCC6872 was suspended in a phosphate buffer (pH 7.0) or citrate buffer (pH 5.5) at a density of $10^7$ cells/mL to $10^8$ cells/mL and treated with UV at room temperature or 32° C. for 20 min to 40 min to induce a mutation. The strain was washed with a 0.85% saline solution twice and spread, after dilution, on a minimal medium containing 1.7% agar which was supplemented with a resistance-providing material at an appropriate concentration, and thereby colonies were obtained. Each colony was cultured in a nutrient medium and then cultured in a seed culture medium for 24 hours. After culturing each colony in a fermentation medium for 3 to 4 days, colonies which showed the most excellent production of IMP accumulated in the culture medium were selected. To prepare a strain producing IMP at high concentration, adenine-auxotroph, guanine-leaky type, lysozyme sensitivity, 3,4-dehydroproline resistance, streptomycin resistance, sulfaguanidine resistance, norvaline resistance, and trimethoprim resistance were provided by performing the corresponding procedures in a sequential manner. As a result, the CJI2332 strain provided with resistance to the above materials and having excellent IMP productivity was finally selected. The resistances of the CJI2332 strain relative to those of ATCC6872 were compared and the results are shown in the following Table 7.

TABLE 7

| Characteristic | ATCC6872 | CJI2332 |
|---|---|---|
| Adenine-auxotroph | Non-auxotroph | Auxotroph |
| Guanine-leaky type | Non-auxotroph | Leaky type |
| Lysozyme sensitivity | 80 µg/mL | 8 µg/mL |
| 3,4-Dehydroproline resistance | 1,000 µg/mL | 3,500 µg/mL |
| Streptomycin resistance | 500 µg/mL | 2,000 µg/mL |
| Sulfaguanidine resistance | 50 µg/mL | 200 µg/mL |
| Norvaline resistance | 0.2 mg/mL | 2 mg/mL |
| Trimethoprim resistance | 20 µg/mL | 100 µg/mL |

Minimal medium: 2% glucose, 0.3% sodium sulfate, 0.1% monopotassium phosphate, 0.3% dipotassium phosphate, 0.3% magnesium sulfate, 10 mg/L calcium chloride, 10 mg/L iron sulfate, 1 mg/L zinc sulfate, 3.6 mg/L manganese chloride, 20 mg/L L-cysteine, 10 mg/L calcium pantothenate, 5 mg/L thiamine hydrochloride, 30 µg/L biotin, 20 mg/L adenine, 20 mg/L guanine, adjusted to pH 7.3.

The CJI2332 strain was deposited at the Korean Culture Center of Microorganisms (KCCM) on Jun. 22, 2018, under the provisions of the Budapest Treaty and assigned accession number KCCM12277P.

Example 4-2: Fermentation Titer Test of CJI2332

After dispensing a seed culture medium (2 mL) into each test tube (diameter: 18 mm), the tubes were autoclaved. Each of ATCC6872 and CJI2332 was inoculated and incubated at 30° C. for 24 hours with shaking and used as a seed culture. A fermentation medium was dispensed (29 mL each) into 250 mL shaking Erlenmeyer flasks and autoclaved at 121° C. for 15 min. The seed culture (2 mL) was inoculated to the medium and cultured for 3 days. Culture conditions were adjusted to 170 rpm, 30° C., and pH 7.5.

After completion of the culture, the amount of IMP production was measured by HPLC (SHIMAZDU LC20A), and the culture results are as in Table 8 below.

TABLE 8

| Strain | IMP (g/L) |
|---|---|
| ATCC6872 | 0 |
| CJI2332 | 1.74 |

Example 4-3: Preparation of Insertion Vector Containing purA Promoter Modification To introduce the modifications selected in Example 3 into the strains, an insertion vector was prepared. The processes for preparing the vector for the introduction of PpurA (c143t), PpurA(a189t), and PpurA(c143t, a1890 modifications are as follows.

PCR was performed using the genomic DNA of the ATCC6872 strain as a template and the primer sets of SEQ ID NOS: 18 and 19 and SEQ ID NOS: 20 and 21. The PCR was performed as follows: denaturation at 94° C. for 5 min; 20 cycles of denaturation at 94° C. for 30 sec, annealing at 55° C. for 30 sec, and polymerization at 72° C. for 1 min; and polymerization at 72° C. for 5 min. PCR was performed again in the same manner using the obtained DNA fragments as a template and the primer set of SEQ ID NOS: 18 and 21, and the thus-obtained gene fragments were each digested with XbaI. Each of the DNA fragments was cloned into a linear pDZ vector digested with XbaI using T4 ligase, and thereby the pDZ-purA(c143t)-purA vector was prepared.

Then, PCR was performed using the genomic DNA of the ATCC6872 strain as a template and the primer sets of SEQ ID NOS: 18 and 22 and SEQ ID NOS: 23 and 21. The PCR was performed as follows: denaturation at 94° C. for 5 min; 20 cycles of denaturation at 94° C. for 30 sec, annealing at 55° C. for 30 sec, and polymerization at 72° C. for 1 min; and polymerization at 72° C. for 5 min. PCR was performed again in the same manner using the obtained DNA fragments as a template and the primer set of SEQ ID NOS: 18 and 21, and the thus-obtained gene fragments were each digested with XbaI. Each of the DNA fragments was cloned into a linear pDZ vector digested with XbaI using T4 ligase, and thereby the pDZ-purA(a189t)-purA vector was prepared.

Additionally, to examine the effect of the introduction of two simultaneous modifications, a vector in which the two modifications were introduced was prepared. Then, site-directed mutagenesis was performed using the prepared pDZ-purA(c143t) as the backbone. Specifically, PCR was performed using the primer sets of SEQ ID NOS: 24 and 25 under the following conditions: 18 cycles of denaturation at 94° C. for 30 sec, annealing at 55° C. for 30 sec, and polymerization at 68° C. for 1 min; and polymerization at 72° C. for 12 min. The obtained PCR products were each digested with DpnI, transformed into DH5a, and thereby the pDZ-PpurA(c143t, a189t)-purA vector was obtained.

pared in Example 1 and the CJI2332 strain selected in Example 4-1, and the amount of IMP produced by each strain was evaluated. To confirm the presence of a modification in the purA promoter of the CJI2332 strain, the genomic DNA of the CJI2332 strain was amplified by PCR. Specifically, first, purA promoter fragments were amplified by PCR using the genomic DNA of the CJI2332 strain as a template and the primer set of SEQ ID NOS: 15 and 21, in which the PCR was performed by 28 cycles of denaturation at 94° C. for 1 min; annealing at 58° C. for 30 sec, and polymerization at 72° C. for 1 min using Taq DNA polymerase. The obtained nucleotide sequences of the amplified purA promoter fragments were analyzed, and as a result, it was confirmed that the nucleotide sequence of the purA promoter of the CJI2332 strain was the same as that of the wild-type *Corynebacterium stationis* ATCC6872.

Then, the pDZ-PpurA(c143t)-purA, pDZ-PpurA(a189t)-purA, and pDZ-PpurA(c143t, a1890-purA vectors were transformed into the CJI2330 strain and the CJI2332 strain, and the strains in which each of the vectors was inserted into the chromosome by recombination of homologous sequences were selected on a medium containing kanamycin (25 mg/L). The selected primary strains were subjected to secondary crossover, and thereby the strains in which a modification in the promoter of a target gene was introduced were selected. For confirmation of the introduction of the gene modification in the final transformed strains, PCR was performed using the primer set of SEQ ID NOS: 15 and 21 and the PCR products were confirmed by analysis of these nucleotide sequences. As a result, it was confirmed that the gene modification was introduced into the strains. The thus-prepared strains were named as CJI2330_PpurA (c143t)-purA, CJI2330_PpurA(a189t)-purA, CJI2330_PpurA(c143t, a189t)-purA, CJI2332_PpurA (c143t)-purA, and CJI2332_PpurA(a189t)-purA, CJI2332_PpurA(c143t, a1890-purA.

The CJI2332_PpurA(c143t)-purA is called CJI2352 and was deposited at the Korean Culture Center of Microorganisms (KCCM) on Sep. 10, 2018, under the provisions of the Budapest Treaty and assigned accession number KCCM12315P. Additionally, the prepared CJI2332_PpurA (a189t)-purA is called CJI2365 and was deposited at the Korean Culture Center of Microorganisms (KCCM) on Sep.

TABLE 9

| SEQ ID NO | Primer | Sequence (5'-3') |
|---|---|---|
| 18 | PDZ purA F | GCTCTAGA ACGGTCACGCGCAAATCAG |
| 19 | purA c143t-1R | CTACCTTTATCGCCAaTGATAATGTATTTAGCCATG |
| 20 | purA c143t-2F | CTAAATACATTATCAtTGGCGATAAAGGTAGAGTT |
| 21 | PDZ purA R | GCTCTAGA TCGTAGGCGACGCAAATAGG |
| 22 | purA a189t-1R | GGTTATTCACTACCTAGATTTAAG |
| 23 | purA a189t-2F | TTAAATCTAGGtAGTGAATAACC |
| 24 | Site-directed mutagenesis F | TAGCCTTAAATCTAGGTAGTGAATAACCATGGCAGCTA |
| 25 | Site-directed mutagenesis R | TAGCTGCCATGGTTATTCACTACCTAGATTTAAGGCTA |

Example 4-4: Introduction of purA Promoter Variants into CJI2330 and CJI2332 Strains Derived from ATCC6872 and Evaluation Thereof The purA promoter modification was introduced to each of the wild-type-derived IMP-producing CJI2330 strain pre- 10, 2018, under the provisions of the Budapest Treaty and assigned accession number KCCM12314P.

The IMP-producing ability of each strain was evaluated. After completion of the culture, the amount of IMP production was measured by a method using HPLC, and the culture results are as in Table 10 below.

TABLE 10

| Strain | IMP (g/L) |
| --- | --- |
| CJI2330 | 0.50 |
| CJI2330_PpurA(c143t)-purA | 0.58 |
| CJI2330_PpurA(a189t)-purA | 0.67 |
| CJI2330_PpurA(c143t, a189t)-purA | 0.72 |
| CJI2332 | 1.74 |
| CJI2332_PpurA(c143t)-purA | 2.01 |
| CJI2332_PpurA(a189t)-purA | 2.29 |
| CJI2332_PpurA(c143t, a189t)-purA | 2.42 |

Example 5: Confirmation of 5'-Xanthylic Acid (XMP)-Producing Ability Upon Introduction of purA Promoter Variant

Example 5-1: Selection of XMP-Producing Strains Derived from ATCC6872

To prepare a 5'-xanthosine monophosphate (XMP)-producing strain derived from ATCC6872, the *Corynebacterium stationis* ATCC6872 strain was suspended in the phosphate buffer (pH 7.0) or citrate buffer (pH 5.5) at a density of $10^7$ cells/mL to $10^8$ cells/mL and treated with UV at room temperature or 32° C. for 20 min to 40 min to induce a mutation. The strain was washed with a 0.85% saline solution twice and spread, after dilution, on a minimal medium containing 1.7% agar which was supplemented with a resistance-providing material at an appropriate concentration, and thereby colonies were obtained. Each colony was cultured in a nutrient medium and then cultured in a seed culture medium for 24 hours. After culturing each colony in a fermentation medium for 3 to 4 days, colonies which showed the most excellent production of XMP accumulated in the culture medium were selected. Specifically, strains were selected from those which can grow in a medium where fluorotryptophan is added according to concentrations (addition medium), and more specifically, from those which can grow in a medium with a fluorotryptophan concentration of 100 mg/L and has an improved concentration of 5'-xanthylic acid. The selected strain was named as CJX1664.

Minimal medium: glucose 20 g/L, monopotassium phosphate 1 g/L, dipotassium phosphate 1 g/L, urea 2 g/L, ammonium sulfate 3 g/L, magnesium sulfate 1 g/L, calcium chloride 100 mg/L, iron sulfate 20 mg/L, manganese sulfate 10 mg/L, zinc sulfate 10 mg/L, biotin 30 µg/L, thiamine hydrochloride 0.1 mg/L, copper sulfate 0.8 mg/L, adenine 20 mg/L, guanine 20 mg/L, pH 7.2

Addition medium: a medium where fluorotryptophan at a concentration of 10 mg/L, 20 mg/L, 50 mg/L, 70 mg/L, 100 mg/L, and 200 mg/L is added to a minimal medium The biochemical characteristics of the CJX1664 strain are shown in Table 11 below. Referring to Table 11, the CJX1664 strain can be grown in an addition medium where fluorotryptophan is added at a concentration of 100 mg/L.

TABLE 11

| Characteristic | ATCC6872 | CJX1664 |
| --- | --- | --- |
| Fluorotryptophan Resistance | 10 mg/L | 100 mg/L |

The CJX1664 strain was deposited at the Korean Culture Center of Microorganisms (KCCM) on Jul. 6, 2018, under the provisions of the Budapest Treaty and assigned accession number KCCM12285P.

Example 5-2: CJX1664 Fermentation Titer Test

After dispensing a seed culture medium (2 mL) into each of the test tubes (diameter: 18 mm), the tubes were autoclaved. Each of ATCC6872 and CJX1664 was inoculated and incubated at 30° C. for 24 hours with shaking and used as a seed culture. A fermentation medium was dispensed (29 mL each) into 250 mL shaking Erlenmeyer flasks and autoclaved at 121° C. for 15 min. The seed culture (2 mL) was inoculated to the medium and cultured for 3 days. Culture conditions were adjusted to 170 rpm, 30° C., and pH 7.5.

After completion of the culture, the amount of XMP production was measured by a method using HPLC (SHIMAZDU LC20A), and the culture results are as in Table 12 below.

TABLE 12

| Strain | XMP (g/L) |
| --- | --- |
| ATCC6872 | 0 |
| CJX1664 | 4.72 |

Example 5-3: Introduction of Variants into CJX1664 Strain and Evaluation Thereof To confirm the presence of a modification in the purA promoter of the CJX1664 strain selected in Example 5-1, the genomic DNA PCR of the CJX1664 strain was amplified by PCR. Specifically, first, purA promoter fragments were amplified by PCR using the genomic DNA of the CJX1664 strain as a template and primers of SEQ ID NOS: 17 and 18, in which the PCR was performed by 28 cycles of denaturation at 94° C. for 1 min; annealing at 58° C. for 30 sec, and polymerization at 72° C. for 1 min using Taq DNA polymerase. The obtained nucleotide sequences of the amplified purA promoter fragments were analyzed, and as a result, it was confirmed that the nucleotide sequence of the purA promoter of the CJI2332 strain was the same as that of the wild-type *Corynebacterium stationis* ATCC6872.

The vectors prepared in Example 4-3 were each transformed into the CJX1664 strain, and the strains in which each of the vectors was inserted into the chromosome by recombination of homologous sequences were selected on a medium containing kanamycin (25 mg/L). The selected primary strains were subjected to secondary crossover, and thereby the strains in which a modification in the promoter of a target gene was introduced were selected. The presence of the introduction of a gene modification in the final transformed strain was confirmed by the analysis of nucleotide sequences.

The XMP-producing abilities of the CJX1664, CJX1664_PpurA(c143t)-purA, CJX1664_PpurA(a189t)-purA, and CJX1664_PpurA(c143t, a1890-purA strains were evaluated. After completion of the culture, the amount of XMP production was measured by a method using HPLC, and the culture results are as in Table 13 below.

The CJX1664_PpurA(c143t)-purA is called CJX1680 and was deposited at the Korean Culture Center of Microorganisms (KCCM) on Sep. 10, 2018, under the provisions of the Budapest Treaty and assigned accession number KCCM12311P. Additionally, the prepared CJX1664_PpurA (a189t)-purA is called CJX1668 and was deposited at the Korean Culture Center of Microorganisms (KCCM) on Sep.

10, 2018, under the provisions of the Budapest Treaty and assigned accession number KCCM12310P.

TABLE 13

| Strain | XMP (g/L) |
| --- | --- |
| CJX1664 | 4.72 |
| CJX1664_PpurA(c143t)-purA | 5.47 |
| CJX1664_PpurA(a189t)-purA | 5.91 |
| CJX1664_PpurA(c143t, a189t)-purA | 6.01 |

As can be seen in Table 13 above, it was confirmed that the CJX1664_PpurA(c143t)-purA, CJX1664_PpurA (a189t)-purA, and CJX1664_PpurA(c143t, a1890-purA strains showed an increase in the amount of XMP production by about 27% compared to the CJX1664 strain (i.e., an ATCC6872-based XMP-producing strain).

From the foregoing, a skilled person in the art to which the present disclosure pertains will be able to understand that the present disclosure may be embodied in other specific forms without modifying the technical concepts or essential characteristics of the present disclosure. In this regard, the exemplary embodiments disclosed herein are only for illustrative purposes and should not be construed as limiting the scope of the present disclosure. On the contrary, the present disclosure is intended to cover not only the exemplary embodiments but also various alternatives, modifications, equivalents, and other embodiments that may be included within the spirit and scope of the present disclosure as defined by the appended claims.

The invention claimed is:

1. A polynucleotide sequence variant of SEQ ID NO: 1 having an activity of a promoter, wherein,
   i) the 143rd nucleotide is substituted with thymine (T);
   ii) the 189th nucleotide is substituted with thymine (T); or
   iii) the 143rd nucleotide is substituted with thymine (T) and the 189th nucleotide is substituted with thymine (T).

2. The polynucleotide according to claim 1, wherein the polynucleotide comprises the nucleotide sequence of SEQ ID NO: 2, SEQ ID NO: 3, or SEQ ID NO: 4.

3. A composition for gene expression comprising the polynucleotide of claim 1.

4. A vector comprising a gene encoding the polynucleotide of claim 1 and a target protein.

5. The vector according to claim 4, wherein the target protein is adenylosuccinate synthetase.

6. A microorganism of the genus Corynebacterium comprising the vector of claim 4.

7. A microorganism of the genus Corynebacterium comprising the gene encoding the polynucleotide of claim 1 and a target protein.

8. The microorganism according to claim 7, wherein the target protein is adenylosuccinate synthetase.

9. The microorganism according to claim 7, wherein the microorganism of the genus Corynebacterium is Corynebacterium stationis.

10. A method for preparing purine nucleotides, comprising culturing the microorganism of the genus Corynebacterium according to claim 7 in a medium.

11. The method according to claim 10, further comprising recovering purine nucleotides from the microorganism or cultured medium after culturing.

12. A microorganism of the genus *Corynebacterium* comprising the vector of claim 5.

* * * * *